US009290814B2

(12) United States Patent
Giafis et al.

(10) Patent No.: US 9,290,814 B2
(45) Date of Patent: Mar. 22, 2016

(54) MATERIALS AND METHODS FOR DIAGNOSIS OF BLADDER CANCER AND MONITORING RECURRENCE THEREOF

(71) Applicant: ABBOTT MOLECULAR INC., Des Plaines, IL (US)

(72) Inventors: Nick Giafis, Chicago, IL (US); Irina Sokolova, Villa Park, IL (US); Minghao Song, Lisle, IL (US); Frank Policht, Niles, IL (US); Svetlana Sitailo, Brookfield, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 70 days.

(21) Appl. No.: 13/721,076

(22) Filed: Dec. 20, 2012

(65) Prior Publication Data

US 2013/0171637 A1    Jul. 4, 2013

Related U.S. Application Data

(60) Provisional application No. 61/581,797, filed on Dec. 30, 2011.

(51) Int. Cl.
*C12Q 1/68* (2006.01)
*C07H 21/02* (2006.01)
*C07H 21/04* (2006.01)

(52) U.S. Cl.
CPC ........ *C12Q 1/6886* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 5,491,224 A | 2/1996 | Bittner et al. | |
| 5,756,696 A | 5/1998 | Gray et al. | |
| 6,008,003 A | 12/1999 | Haak-Frendscho et al. | |
| 6,573,042 B1 | 6/2003 | Wang | |
| 6,582,908 B2 * | 6/2003 | Fodor et al. | 506/9 |
| 6,759,204 B2 | 7/2004 | Benistant et al. | |
| 6,951,926 B2 | 10/2005 | Getzenberg | |
| 6,960,443 B2 | 11/2005 | Reiter et al. | |
| 6,998,232 B1 | 2/2006 | Feinstein et al. | |
| 7,011,950 B2 | 3/2006 | Yung | |
| 7,135,549 B1 | 11/2006 | Challita-Eid et al. | |
| 7,153,700 B1 | 12/2006 | Pardee et al. | |
| 7,192,711 B2 | 3/2007 | Olopade | |
| 7,223,542 B2 | 5/2007 | Raitano et al. | |
| 7,232,655 B2 † | 6/2007 | Halling | |
| 7,374,897 B2 | 5/2008 | Yuan | |
| 7,374,902 B2 | 5/2008 | Yuan | |
| 7,563,444 B2 | 7/2009 | Challita-Eid et al. | |
| 7,759,077 B2 | 7/2010 | Shariat | |
| 7,776,518 B2 | 8/2010 | Altieri et al. | |
| 7,794,926 B2 | 9/2010 | Altieri et al. | |
| 7,842,458 B2 | 11/2010 | Kanner et al. | |
| 7,862,997 B2 | 1/2011 | Daitho | |
| 7,879,570 B2 | 2/2011 | Challita-Eid et al. | |
| 7,910,316 B2 | 3/2011 | Akiyama et al. | |
| 2005/0252773 A1 | 11/2005 | McBride et al. | |
| 2009/0069194 A1 | 3/2009 | Ramakrishnan | |
| 2013/0078632 A1 * | 3/2013 | Krishnadath | 435/6.11 |

FOREIGN PATENT DOCUMENTS

| | | |
|---|---|---|
| EP | 1035215 A2 | 9/2000 |
| EP | 1035215 B1 | 7/2006 |
| EP | 2138848 A1 | 12/2009 |
| EP | 2138848 B1 | 11/2010 |
| JP | 2000131321 A | 5/2000 |
| JP | 2002238599 A | 8/2002 |
| JP | 2004061288 A | 2/2004 |
| JP | 2004248508 A | 9/2004 |
| JP | 2004337120 A | 12/2004 |
| WO | 9318186 A1 | 9/1993 |
| WO | 9617958 A1 | 6/1996 |
| WO | 2010055467 A1 | 5/2010 |

OTHER PUBLICATIONS

Affymetrix GeneChip® Human Genome U133 Plus 2.0 Array (Affymetrix Package Insert for the HG-U133 Plus 2.0 Array, 2003, available via url: <media.affymetrix.com/support/downloads/package_inserts/hgu133_plus_insert.pdf>.*
Ahern, H. The Scientist. Jul. 1995. 9(15): 20-25.*
Zaharieva et al. Int J Cancer. 2003. 117:952-956I.*
Andy Choo K.H., ed., In Situ Hibridization Protocols: Methods in Molecular Biology, vol. 33, Humana Press Inc., 1994, Table of Contents.
Carter N.P., "Methods and Strategies for Analyzing Copy Number Variation Using DNA Microarrays," Nature Genetics, 2007, vol. 39 (Suppl. 7), pp. S16-S21.
Herrick J., et al., "Quantifying Single Gene Copy Number by Measuring Fluorescent Probe Lengths on Combed Genomic DNA,"Proceedings of the National Academy of Sciences, 2000, vol. 97 (1), pp. 222-227.
International Search Report and Written Opinion for Application No. PCT/US2012/070745, mailed on Feb. 5, 2013, 12 pages.
Kallioniemi A., et al., "Comparative Genomic Hybridization for Molecular Cytogenetic Analysis of Solid Tumors," Science, 1992, vol. 258 (5083), pp. 818-821.

(Continued)

*Primary Examiner* — Carla Myers
(74) *Attorney, Agent, or Firm* — Lisa V. Mueller; Michael Best & Friedrich LLP

(57) ABSTRACT

A method of diagnosing bladder cancer in a patient comprising contacting a sample of urothelial cells obtained from the patient with a set of detectably labeled probes comprising locus-specific probes for c-myc and AURKA and centromeric probes for chromosomes 7 and 17 under hybridization conditions, and determining the presence of chromosomal abnormalities, wherein the presence of chromosomal abnormalities involving at least two of the detectably labeled probes indicates that the patient has bladder cancer; a method of monitoring recurrence of bladder cancer in a patient; a set of probes comprising locus-specific probes for c-myc and AURKA and centromeric probes for chromosomes 7 and 17; and a kit comprising (a) the set of probes and (b) instructions for diagnosing bladder cancer, or monitoring the recurrence thereof, in a patient.

6 Claims, No Drawings

(56) References Cited

OTHER PUBLICATIONS

Kallioniemi A., et al., "Identification of Gains and Losses of DNA Sequences in Primary Bladder Cancer by Comparative Genomic Hybridization," Genes Chromosomes & Cancer, 1995, vol. 12 (3), pp. 213-219.

Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.

Kumar J., et al., "Detection of Differential Gene Copy Number Using Denaturing High Performance Liquid Chromatography," Journal of Biochemical and Biophysical Methods, 2005, vol. 64 (3), pp. 226-234.

Leonard C., et al., [From Cytogenetics to Cytogenomics of Bladder Cancers], Bulletin du Cancer, 2002, vol. 89 (2), pp. 166-173.

Liu Z., et al., "Simple Copy Number Determination with Reference Query Pyrosequencing (RQPS)," Cold Spring Harbor Protocols, 2010, vol. 2010 (9), 10 pages.

Morrison, L.E. et al., "Labeling Fluorescence In Situ Hybridization Probes for Genomic Targets," Methods in Molecular Biology, 2002, vol. 204, pp. 21-40.

Mourah S., et al., "Assessment of Microsatellite Instability in Urine in the Detection of Transitional-Cell Carcinoma of the Bladder," International Journal of Cancer, 1998, vol. 79 (6), pp. 629-633.

Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.

Rigby P.W., et al., "Labeling Deoxyribonucleic Acid to High Specific Activity in Vitro by Nick Translation with DNA Polymerase I," Journal of Molecular Biology, 1977, vol. 113 (1), pp. 113-237.

Sambrook J., et al., eds., Molecular Cloning: A Laboratory Manual, 3rd Edition, Cold Spring Harbor Laboratory, 2001, Table of Contents.

Schouten J.P., et al., "Relative Quantification of 40 Nucleic Acid Sequences by Multiplex Ligation-dependent Probe Amplification," Nucleic Acids Research, 2002, vol. 30 (12), pp. e57.

Service R.F., "Gene Sequencing. The Race for the $1000 Genome," Science, 2006, vol. 311 (5767), pp. 1544-1546.

Shendure J., et al., "Advanced Sequencing Technologies: Methods and Goals," Nature Reviews. Genetics, 2004, vol. 5 (5), pp. 335-344.

Song M.J., et al., "Clinical Usefulness of Fluorescence in Situ Hybridization for Diagnosis and Surveillance of Bladder Cancer," Cancer Genetics and Cytogenetics, 2010, vol. 198 (2), pp. 144-150.

Tijssen P., "Hybridization with Nucleic Acid Probes" in: Laboratory Techniques in Biochemistry and Molecular Biology, vol. 24, Chapter 2, Van der Vliet P.C., ed., Elsevier Publisher, 1993, pp. 19-78.

Veltman J.A., et al., "Array-based Comparative Genomic Hybridization for Genome-Wide Screening of DNA Copy Number in Bladder Tumors," Cancer Research, 2003, vol. 63 (11), pp. 2872-2880.

Vogelstein B., et al., "Digital PCR," Proceedings of the National Academy of Sciences, 1999, vol. 96 (16), pp. 9236-9241.

Yamashita, et al., "Chromosomal Numerical Abnormality Profiles of Gastrointestinal Stromal Tumors," Jpn. J. Clin. Oncol., vol. 36, No. 2, pp. 85-92 (2006).†

Park, H-S., et al., "Quantitation of Aurora Kinase A Gene Copy Number in Urine Sediments and Bladder Cancer Detection," J. Natl. Cancer Inst., vol. 100, Issue 19, pp. 1401-1411 (2008).†

Lassmann, S., et al., "Predictive Value of Aurora-A/STK15 Expression for Late Stage Epithelial Ovarian Cancer Patients Treated by Adjuvant Chemotherapy," Clin. Cancer Res., vol. 13, No. 14, pp. 4083-4091 (2007).†

Chan, J.Y., et al., "A Clinical Overview of Centrosome Amplification in Human Cancers," Int. J. Biol. Sci., vol. 7, pp. 1122-1144 (2011).†

Baffa, R., "Molecular Genetics of Bladder Cancer: Targets for Diagnosis and Therapy," J. Exp. Clin. Cancer Res., vol. 25, No. 2, pp. 145-160 (2006).†

FISH Catalogue Supplement 2006, published by MP Biomedicals, LLC, United States.†

\* cited by examiner
† cited by third party

MATERIALS AND METHODS FOR DIAGNOSIS OF BLADDER CANCER AND MONITORING RECURRENCE THEREOF

CROSS REFERENCE TO RELATED APPLICATIONS

This application claims priority to U.S. provisional patent application No. 61/581,797, which was filed on Dec. 30, 2011, and the content of which is hereby incorporated by reference in its entirety.

TECHNICAL FIELD

The present disclosure relates to the diagnosis of bladder cancer and the monitoring of the recurrence thereof, the determination of chromosomal abnormalities, and in situ hybridization, as well as a set of probes and a kit useful for diagnosis of bladder cancer.

BACKGROUND

Bladder cancer often develops in people aged fifty and older. Men develop bladder cancer at a rate 2 to 3 times higher than that for women. Also, smokers are approximately four times more likely to develop bladder cancer than nonsmokers.

Bladder cancer is roughly classified into two types, i.e., superficial bladder cancer and infiltrative bladder cancer. Superficial bladder cancer is characterized by shallow papillary tumors that protrude out from the inner surface of the bladder and relatively low malignancy. Superficial bladder cancer can be treated endoscopically, although it recurs in the bladders of half or more patients. In contrast, infiltrative bladder cancer is characterized by deep infiltration, such as the bladder wall, and metastasis to other parts of the body. Infiltrative bladder cancer can be treated by bladder extirpation, chemotherapy, and radiotherapy.

The most common sign of bladder cancer is painless hematuria; however, symptoms may be similar to those of cystitis, such as increased urinary frequency, pain during urination, or the feeling of incomplete emptying of the bladder. Diagnosis of bladder cancer is carried out by urine analysis (cytological diagnosis), x-ray imaging, or endoscopy.

Due to a lack of specific and highly sensitive tumor markers for early diagnosis, such as by assay of urine or blood, bladder cancer is often detected after the cancer has progressed. Accordingly, practical application of a simple detection method with the use of specific and highly sensitive tumor markers for urothelial cancer, and particularly for bladder cancer, is desired.

A variety of markers and methods have been proposed for diagnosis of bladder cancer. Examples include the detection of changes in expression levels of genes, such as nucleophosmin/B23 (JP Patent Publication (kokai) No. 2004-337120 (A)), HURP (JP Patent Publication (kokai) No. 2004-248508 (A)), and CYP4B1 or CYP4B2 (JP Patent Publication (kokai) No. 2002-238599 (A)), the detection of changes in the level of a given protein in urine (JP Patent Publication (kokai) Nos. 2004-61288 (A) and H7-309895 (1995)(A)), and the detection of changes in the level of soluble Fas in blood or urine (JP Patent Publication (kokai) No. 2000-131321 (A); and U.S. Pat. No. 7,759,077). More recently, the detection of an increase in the level of CXCL1 protein (see U.S. Pat. No. 7,910,316), the detection of an increase in the level of 184P1E2 protein (see U.S. Pat. Nos. 7,879,570 and 7,135,549), the detection of the presence of carcinoembryonic antigen (CEA; see U.S. Pat. No. 7,862,997), the detection of an increase in the level of 58P1D12 protein (see U.S. Pat. No. 7,842,458), the detection of the presence of survivin (see U.S. Pat. Nos. 7,794,926 and 7,776,518), the detection of an increase in the level of 213P1F11 (see U.S. Pat. No. 7,563,444), the assay of α-methylacyl-CoA racemase activity (see U.S. Pat. Nos. 7,374,902 and 7,374,897), the detection of an increase in the level of 36P6D5 (see U.S. Pat. No. 7,223,542), the absence of methylthioadenosine phosphorylase (MTAP; see U.S. Pat. No. 7,192,711), the detection of an increase in the level of SIX1 (U.S. Pat. No. 7,153,700), the detection of an increase in the level of nucleophosmin/B23 (see U.S. Pat. No. 7,011,950), the detection of increases in the levels of syndecan-1 and hepatocyte growth factor activator-inhibitor type 2 (see U.S. Pat. No. 6,998,232), the detection of an increase in prostate stem cell antigen (see U.S. Pat. No. 6,960,443), the detection of the presence of BLCA-6 (see U.S. Pat. No. 6,951,926), the detection of the presence of anti-Csk auto-antibodies (see U.S. Pat. No. 6,759,204), the detection of a change in the number of chromosomes 1, 7, 8, 9, 10, 11, Y and/or X (see U.S. Pat. No. 6,573,042), the detection of the level of neurotrophin-3, nerve growth factor, glial cell line-derived neurotrophic factor, and/or tryptase in urine (see U.S. Pat. No. 6,008,003), and the detection and quantification of expression of ANXA10, C14orf78, CTSE, CRH, IGF2, KLF9, KRT20, MAGEA3, POSTN, PPP1R14D, SLC1A6, TERT, ASAM, and MCM10 (see European Pat. App. Pub. No. EP 2138848), have been proposed. The detection of aneusomic cells using a probe set consisting of centromeric probes for chromosomes 3, 7 and 17 and the locus-specific probe 9p21 has been proposed as useful for monitoring recurrence and need for continued treatment (see U.S. Pat. No. 7,232,655).

The present disclosure seeks to provide a set of markers, as well as methods of use and a kit, for the detection of bladder cancer, particularly in patients who have symptoms of bladder cancer or have recurrent bladder cancer, and the monitoring of the recurrence of bladder cancer. This and other objects and advantages, as well as inventive features, will become apparent from the detailed description provided herein.

SUMMARY

A method of diagnosing bladder cancer in a patient is provided. The method comprises contacting a sample of urothelial cells obtained from the patient with a set of detectably labeled probes under hybridization conditions. The set of detectably labeled probes comprises a locus-specific probe for c-myc, a locus-specific probe for AURKA, a centromeric probe for chromosome 7, and a centromeric probe for chromosome 17. The method also comprises determining the presence of chromosomal abnormalities. The presence of chromosomal abnormalities involving at least two of the detectably labeled probes indicates that the patient has bladder cancer.

A method of monitoring the recurrence of bladder cancer in a patient is also provided. The method comprises contacting a sample of urothelial cells obtained from the patient with a set of detectably labeled probes under hybridization conditions. The set of detectably labeled probes comprises a locus-specific probe for c-myc, a locus-specific probe for AURKA, a centromeric probe for chromosome 7, and a centromeric probe for chromosome 17. The method also comprises determining the presence of chromosomal abnormalities. The presence of chromosomal abnormalities involving at least two of the detectably labeled probes indicates that bladder cancer has recurred in the patient.

A set of probes is also provided. The set of probes comprises a locus-specific probe for c-myc, a locus-specific probe for AURKA, a centromeric probe for chromosome 7, and a centromeric probe for chromosome 17.

Also provided is a kit. The kit comprises a set of probes that enables diagnosis of bladder cancer, or monitoring of the recurrence thereof, in a patient and instructions for diagnosing bladder cancer, or monitoring the recurrence thereof, in a patient. The set of probes comprises a locus-specific probe for c-myc, a locus-specific probe for AURKA, a centromeric probe for chromosome 7, and a centromeric probe for chromosome 17. The instructions comprise determining in a sample of urothelial cells obtained from the patient the presence of chromosomal abnormalities. The presence of chromosomal abnormalities involving at least two of the probes indicates that the patient has bladder cancer.

DETAILED DESCRIPTION

The present disclosure provides a set of markers, as well as methods of use and a kit, for the detection of bladder cancer, particularly in patients who have symptoms of bladder cancer or have recurrent bladder cancer, and the monitoring of the recurrence of bladder cancer. The method enables the detection of bladder cancer in its earliest stages.

The following terms are relevant to the present disclosure:

"About" refers to approximately a +/−10% variation from the stated value. It is to be understood that such a variation is always included in any given value provided herein, whether or not specific reference is made to it.

"Bladder cancer" is cancer that forms in the tissues of the bladder. Bladder cancer is used herein to include transitional cell carcinoma (TCC), which is also referred to as urothelial cell carcinoma, squamous cell carcinoma, and adenocarcinoma.

"Biomarker," as defined by the National Institutes of Health, is "a characteristic that is objectively measured and evaluated as an indicator of normal biologic processes, pathogenic processes, or pharmacologic responses to a therapeutic intervention."

"Chromosome enumeration probe (CEP)" or "centromeric probe" is any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.).

"Copy number" is a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" refers to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+)

strand of DNA or complementary to the non-coding or antisense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications, whereas a length of about 50-1×10$^5$ nucleotides can be preferred for chromosomal probes and a length of about 25,000 to about 800,000 nucleotides can be preferred for locus-specific probes.

"Selectively hybridize to" (as well as "selective hybridization," "specifically hybridize to," and "specific hybridization"), in the context of the present disclosure, refers to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, N.Y. (1993) ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual*, 3rd ed., Vol. 1-3, Cold Spring Harbor Laboratory, Cold Spring Harbor Press, N.Y. (2001)).

"Target sequence," "target region," and "nucleic acid target" refer to a nucleotide sequence that resides at a specific chromosomal location whose loss and/or gain, for example, is being determined.

The terminology used herein is for the purpose of describing particular embodiments only and is not otherwise intended to be limiting.

Method of Diagnosing Bladder Cancer

A method of diagnosing bladder cancer in a patient, such as a patient with hematuria and/or other signs and/or symptoms of bladder cancer, is provided. The method comprises contacting a sample of urothelial cells obtained from the patient with a set of detectably labeled probes comprising, or consisting of, a locus-specific probe for c-myc (8q24), a locus-specific probe for Aurora kinase (AURKA; 20q13, specifically 20q13.2), a centromeric probe for chromosome 7, and a centromeric probe for chromosome 17 under hybridization conditions, and determining the presence of chromosomal abnormalities. The presence of chromosomal abnormalities involving at least two of the detectably labeled probes indicates that the patient has bladder cancer. Thus, in view of the foregoing, the detection of chromosomal abnormalities involving c-myc (8q24) and Aurora kinase (AURKA; 20q13); c-myc (8q24) and chromosome 7; c-myc (8q24) and chromosome 17; AURKA (20q13) and chromosome 7; AURKA (20q13) and chromosome 17; chromosome 7 and chromosome 17; c-myc (8q24), AURKA (20q13), and chromosome 7; c-myc (8q24), AURKA (20q13), and chromosome 17; AURKA (20q13), chromosome 7, and chromosome 17; chromosome 7, chromosome 17, and c-myc (8q24); or c-myc (8q24), AURKA (20q13), chromosome 7, and chromosome 17 indicate that the patient has bladder cancer.

The method can be used to detect or monitor recurrent bladder cancer. Thus, a method of monitoring recurrence of bladder cancer in a patient is also provided. The method comprises contacting a sample of urothelial cells obtained from the patient with a set of detectably labeled probes under hybridization conditions. The set of detectably labeled probes comprises, or consists of, a locus-specific probe for c-myc, a locus-specific probe for AURKA, a centromeric probe for chromosome 7, and a centromeric probe for chromosome 17. The method also comprises determining the presence of chromosomal abnormalities. The presence of chromosomal abnormalities involving at least two of the detectably labeled probes indicates that bladder cancer has recurred in the patient. Thus, in view of the foregoing, the detection of chromosomal abnormalities involving c-myc (8q24) and Aurora kinase (AURKA; 20q13); c-myc (8q24) and chromosome 7; c-myc (8q24) and chromosome 17; AURKA (20q13) and chromosome 7; AURKA (20q13) and chromosome 17; chromosome 7 and chromosome 17; c-myc (8q24), AURKA (20q13), and chromosome 7; c-myc (8q24), AURKA (20q13), and chromosome 17; AURKA (20q13), chromosome 7, and chromosome 17; chromosome 7, chromosome 17, and c-myc (8q24); or c-myc (8q24), AURKA (20q13), chromosome 7, and chromosome 17 indicate that bladder cancer has recurred in the patient. Generally, for assays in which repeat testing may be done (e.g., monitoring recurrence of disease), a second or subsequent test sample is obtained at a period in time after the first test sample has been obtained from the subject. Specifically, a second test sample from the subject can be obtained weeks or years after the first test sample has been obtained from the subject. For example, the second test sample can be obtained from the subject at a time period of about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

The above method can be carried out using any suitable detection method known in the art. Preferably, the above method is carried out using in situ hybridization, such as fluorescent in situ hybridization (FISH). Preferably, each probe is detectably labeled with a distinct label, such as a distinct fluorophore. When the above methods are carried out by in situ hybridization, in which each probe is detectably labeled (and, when two or more probes are used simultaneously or sequentially with the same sample, distinctly labeled), such as by FISH, in which each probe is labeled with a fluorophore, the methods are typically carried out on a sample of urothelial cells, which are obtained from a voided urine sample or, alternatively, a bladder washing (e.g., with water or saline). If the cells are obtained from a urine sample, preferably the urine sample is obtained from the patient's first morning urine. The cells contained in the urine or bladder washing can be harvested in any suitable manner known in the art. Preferably, the cells are harvested by centrifugation and resuspension of the pelleted cells. Typically, the cells are resuspended in phosphate-buffered saline (PBS). Once the cells are harvested, they can be prepared for in situ hybridization in accordance with methods well-known in the art. The cells can be analyzed within a short time after harvesting. Alternatively, cells can be fixed (e.g., in acid alcohol solution, such as methanol:glacial acetic acid (3:1), acid acetone solution, aldehydes, such as formaldehyde, paraformaldehyde, and glutaraldehyde, or a neutral buffered formalin solution (formaldehyde in an aqueous solution of sodium phosphate)) and analyzed at a later time. If desired, fresh (fresh cells can be cultured for 1-3 days and a blocker, such as Colcemid, can be added to the culture to block the cells in metaphase, during which chromosomes are highly condensed and can be visualized), frozen, or fixed (e.g., fixed in ethanol or formalin and embedded in paraffin) cells can be treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a cell suspension can be applied as a single layer onto a solid support suitable for examination by microscopy, such as a slide or a coverslip, and the cell density can be measured by a light or phase contrast microscope. A voided urine specimen that is collected and fixed in a solution such as PreservCyt can be deposited onto a slide (UroCyte, available from Hologic, Marlborough, Mass.) using a cell deposition system such as the ThinPrep 2000. Slides can be prepared and soaked in 95% dehydrant for 30 minutes at room temperature. Afterwards, the slides can be dried in a vertical position on a bench top for about 30 minutes to one hour before hybridization. The slide is then pretreated in 2× saline sodium citrate (SSC) at 72° C. for about 2 minutes and digested with protease (0.1-0.5 mg/mL in 10 mM HCl) at 37° C. for about 10 minutes. Following protease digestion, the slide can be rinsed in 1× phosphate-buffered saline (PBS) for about five minutes at room temperature, fixed in 1% neutral-buffered formalin solution for about five minutes at room temperature, rinsed again in 1×PBS for about five minutes at room temperature, passed through graded ethanol, and dried. Preferably, the slide is contacted with one or more probes co-denatured at 73° C. for about two minutes on a Thermo-Brite Denaturation/Hybridization System (Abbott Molecular, Inc., Des Plaines, Ill.) and hybridized at 37° C. overnight (about 16-24 hours). After hybridization, the coverslips are removed from the slides and the slides are then immersed in a primary washing buffer for about five minutes at 73° C. and then a secondary washing buffer for about one minute at room temperature. The slides are then dried and mounted with 4'6'diamidino-2-phenylindole dihydrochloride hydrate (DAPI) II anti-fade solution (Abbott Molecular, Inc.). Preferably, the slide is analyzed with an epi-fluorescence microscope equipped with single band-pass filters (Abbott Molecular, Inc.).

Alternatively, a section (approximately 5 μm in thickness) of a formalin-fixed, paraffin-embedded (FFPE) sample of urothelial cells (e.g., from a suspected tumor) can be mounted onto a slide, such as a SuperFrost Plus positively charged slide (available from ThermoShandon, Pittsburgh, Pa.), baked at 56-60° C. overnight, de-paraffinized using Hemo-De, CtriSolv, or xylene for five minutes, submerged in 1× saline sodium citrate, pH 6.3, at 80° C. for 35 minutes, and washed in water for three minutes. After protease digestion (1-4 mg pepsin/mL, such as 1.5 mg pepsin/mL, and dissolved in 0.1-0.2 N HCl) at 37° C. for 15 minutes, the section can be rinsed in water for three minutes, passed through graded ethanol, and dried. Preferably, hybridization with one or more probes as described above is carried out at 37° C. for 16-24 hours in an automated co-denaturation oven (HYBrite or ThermoBrite Denaturation/Hybridization System, Abbott Molecular, Inc., Des Plaines, Ill.) according to the manufacturer's instructions (such methods typically involve denaturation of probes and target nucleic acids). After hybridization, the section is preferably placed in washing buffer (2× saline sodium citrate/0.3% NP40; available from Abbott Molecular, Inc.) at room temperature for 2-10 minutes to remove the coverslip and then immersed in 73° C. washing buffer for two minutes, dried, and mounted with 4'6'-diamidino-2-phenylindole dihydrochloride hydrate (DAPI) I anti-fade solution (Abbott Molecular, Inc.). Preferably, the slide is analyzed with an epi-fluorescence microscope equipped with single band-pass filters (Abbott Molecular, Inc.).

Prior to detection, cells in a sample may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. During pre-selection, cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes, such as propidium iodide or 4,6-diamidino-2-phenylindole dihydrochloride (DAPI), usually following hybridization of probes to their target DNAs. Typically, neoplastic cells harbor nuclei that are enlarged, irregular in shape, and/or show a mottled nuclear staining pattern. Propidium iodide, typically used at a concentration of about 0.4 μg/ml to about 5 μg/ml, is a red-fluorescing DNA-specific dye that can be observed at an emission peak wavelength of 614 nm. DAPI, typically used at a concentration of about 125 ng/ml to about 1,000 ng/ml, is a blue fluorescing DNA-specific stain that can be observed at an emission peak wavelength of 452 nm with a DAPI filter at low magnification. In this case, only those cells pre-selected for detection are subjected to counting for chromosomal losses and/or gains. Preferably, pre-selected cells on the order of at least 20, and more preferably at least 30-40, in number are chosen for assessing chromosomal losses and/or gains.

Alternatively, an area evidencing some level of dysplasia or a suspicious lesion can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, three abnormal areas are selected and, within each abnormal area, 10 random nuclei are analyzed under high power (60× or 100× objective). Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

The copies of c-myc (8q24), AURKA (20q13), chromosome 7, and chromosome 17 are counted and recorded. The presence of chromosomal abnormalities involving at least two of c-myc, AURKA, chromosome 7, and chromosome 17 indicates that the patient has bladder cancer.

Thus, such methods comprise contacting a sample of urothelial cells obtained from a patient, e.g., a nucleic acid sample, with a set of detectably labeled probes comprising a locus-specific probe for c-myc (8q24), a locus-specific probe for AURKA (20q13), a centromeric probe for chromosome 7, and a centromeric probe for chromosome 17 under conditions that allow (or promote) the probe to bind selectively with its target nucleic acid sequence and form a stable hybridization complex. Such methods further comprise detecting the formation of the hybridization complex and counting the number of hybridization complexes. In view of the number of hybridization complexes comprising c-myc (8q24), AURKA (20q13), chromosome 7, and chromosome 17, the method further comprises determining the copy number of c-myc (8q24), AURKA (20q13), chromosome 7, and chromosome 17. If desired, the copy number can be compared to a pre-determined cut-off, wherein a copy number greater than the pre-determined cut-off (i.e., for a gain) and a copy number less than the pre-determined cut-off (i.e., for a loss), as appropriate, indicates that the patient has bladder cancer.

While deparaffinization, pretreatment, staining, and routine slide washing also can be conducted in accordance with methods known in the art, use of an automated system, however, such as the VP 2000 Processor (Abbott Molecular, Inc., Des Plaines, Ill.), decreases the amount of time needed to prepare slides for evaluation. Slides can be prepared in large batches (e.g., 50 slides), as opposed to small batches (e.g., 4 slides) when standard Coplin jars are used for post-hybridization washing. In addition, the scoring of slides can be fully automated using automated imaging, thereby reducing the amount of hands-on time required for specimen analysis. Full automation also enables the use of an imaging algorithm that captures more abnormal cells more frequently and consistently. Also, while any suitable method of slide preparation known in the art can be used, slides are preferably prepared using ThinPrep 2000 (Hologic, Inc., Bedford, Mass.), which generates more uniform and consistent monolayers of cells.

Other methods already known in the art or currently under development may necessitate the use of a sample of urothelial cells that is other than cells fixed in formalin and embedded in paraffin, e.g., fresh or frozen cells, homogenized cells, lysed cells, or isolated or purified nucleic acids (e.g., a "nucleic acid sample" such as DNA) from urothelial cells ("sample of urothelial cells" as used herein is intended to encompass all forms of a sample of urothelial cells that enable the determination of copy number and gain/loss). Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dHPLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step can precede contact of the probes with the targets. Alternatively, the probe and the target can be subjected to denaturing conditions together while in contact with one another, or with subsequent contact of the probe with the biological sample. Hybridization can be achieved with subsequent incubation of the probe/sample in, for example, a liquid phase of about a 50:50 volume ratio mixture of 2-4× SSC and formamide, at a temperature in the range of about 25 to about 55° C. for a time that is illustratively in the range of about 0.5 to about 96 hours, or more preferably at a temperature of about 32 to about 42° C. for a time in the range of about 2 to about 24 hours. In order to increase specificity, a blocking agent, such as unlabeled blocking nucleic acid, as described in U.S. Pat. No. 5,756,696 (the contents of which are herein incorporated by reference in their entirety, and specifically for the description of the use of blocking nucleic acid), can be used. Other conditions can be readily employed for specifically hybridizing the probes to their nucleic acid targets present in the sample, as would be readily apparent to one of skill in the art. Hybridization protocols are described, for example, in Pinket et al., PNAS USA 85: 9138-9142 (1988); In situ Hybridization Protocols, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA can be removed by a series of washes. Temperature and salt concentrations are suitably chosen for a desired stringency. The level of stringency required depends on the complexity of a specific probe sequence in relation to the genomic sequence, and can be determined by systematically hybridizing probes to samples of known genetic composition. In general, high stringency washes can be carried out at a temperature in the range of about 65 to about 80° C. with about 0.2× to about 2×SSC and about 0.1% to about 1% of a non-ionic detergent, such as Nonidet P-40 (NP40). If lower stringency washes are required, the washes can be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method can be used in conjunction with the methods described herein for observing multiple fluorophores. In the case where fluorescence microscopy is employed, hybridized samples can be viewed under light suitable for excitation of each fluorophore and with the use of an appropriate filter or filters. Automated digital imaging systems, such as the MetaSystems, BioView, Leica, Ikonisys, or Applied Imaging systems, alternatively can be used.

Depending on the method employed, a digital image analysis system can be used to facilitate the display of results and to improve the sensitivity of detecting small differences in fluorescence intensity. An exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display, which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

In view of the above, a manual procedure can involve collecting cells from urine and fixing them in Carnoy's reagent. Twelve-well slides can be prepared containing 3 µL, 10 µL and 30 µL drops of a sample of cell suspension. The slides can be pre-treated manually (optionally, pre-treated using VP2000 (Abbott Molecular, Inc., Des Plaines, Ill.)), hybridized manually (optionally, hybridized using Thermobrite Denaturation/Hybridization System (Abbott Molecular, Inc.)), and washed manually. Using microscopy, abnormal cells can be selected, and probes can be enumerated. Preferably, an automated procedure is used. An automated procedure can involve collecting cells from urine and fixing them in PreservCyt (Hologic, Inc., Bedford, Mass.). ThinPrep slides (Hologic, Inc.) can be prepared, pre-treated using VP2000 (Abbott Molecular, Inc.), and hybridized using Thermobrite Denaturation/Hybridization System (Abbott Molecular, Inc.). The slides can be washed and, using microscopy, abnormal cells can be identified, and probes can be enumerated. Cells can be pre-scanned, sorted and imaged, which allows for automatic probe enumeration and remote review. The use of ThinPrep results in cleaner background, reduced cell loss, larger and flatter cell morphology, and better signal quality.

Probes

A set of probes is also provided. The set of probes comprises, or consists of, a locus-specific probe for c-myc, a locus-specific probe for AURKA, a centromeric probe for chromosome 7, and a centromeric probe for chromosome 17.

Suitable probes for use as locus-specific probes hybridize to a specific region on a chromosome containing a gene. The locus-specific probe for the gene c-myc (8q24) can hybridize to all or a portion of the c-myc gene at q24 on chromosome 8 (i.e., 8q24). The locus-specific probe for the gene AURKA (20q13) can hybridize to all or a portion of the AURKA gene at q13 on chromosome 20 (i.e., 20q13, specifically 20q13.2). A clone for AURKA is available from M.D. Anderson Cancer Center at the University of Texas. Alternatively, a probe that hybridizes to all or portion of 20q13 and an adjacent region on either or both sides of 20q13 can be used. Such a probe, for example, can hybridize to all or a portion of the 17.5 kb ZNF217 gene and/or all or a portion of the D20S108 locus, which is located at 20q12.

Suitable probes for use as chromosomal probes hybridize with repetitive DNA associated with the centromere of a chromosome. Centromeres of primate chromosomes contain a complex family of long-tandem repeats of DNA, which are composed of a monomer repeat length of about 171 base pairs (bp), that is referred to as α-satellite DNA. Chromosomal probes are typically about $50\text{-}1\times10^5$ nucleotides in length. Longer probes typically comprise smaller fragments of about 100-500 nucleotides in length. The probe for chromosome 7 can hybridize to the alpha satellite DNA located at the centromere of chromosome 7, whereas the probe for chromosome 17 can hybridize to the alpha satellite DNA located at the centromere of chromosome 17. Examples of such probes include CEP7 and CEP17.

Chromosome enumerator probes (CEP) and locus-specific probes that target a chromosome region or subregion can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. In another embodiment, the chromosomal probes can be oligo probes. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., c-myc.

The probes can be prepared by any method known in the art. Probes can be synthesized or recombinantly produced.

Preferably, probes are detectably labeled, and, when two or more probes are used simultaneously or sequentially on the same sample, preferably each probe is distinctly labeled. Preferably, the probes are detectably labeled with fluorophores, and, when two or more probes are used simultaneously or sequentially on the sample sample, preferably each probe is distinctly labeled with a fluorophore. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, SpectrumRed (Abbott Molecular, Inc.), SpectrumGold (Abbott Molecular, Inc.), SpectrumGreen (Abbott Molecular, Inc.), SpectrumAqua (Abbott Molecular, Inc.), TEXAS RED (Molecular Probes, Inc.), Lucifer yellow, and CASCADE blue acetylazide (Molecular Probes, Inc.). The particular label used is not critical; desirably, however, the particular label does not interfere with in situ hybridization of the probe and the detection of label on any other probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, end labeling, direct labeling by chemical modification of particular residues, such as cytosine residues (U.S. Pat. No. 5,491,224), and the like. Alternatively, the fluorophore can be covalently attached to nucleotides with activated linker arms, which have been incorporated into the probe, for example, via a linker to the deoxycytidine nucleotides of the probe that have been transaminated. Methods for labeling probes are described in U.S. Pat. No. 5,491,224, and Morrison et al., Molecular Cytogenetics: Protocols and Applications, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label-containing moieties. Agents that are detectable with visible light include cyanin dyes. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions alternatively can be visualized by enzymatic reactions of label moieties with suitable substrates for the production of insoluble color products. Each probe can be discriminated from other probes within the set by choice of a distinct label moiety. A biotin-containing probe within a set can be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kit

Also provided is a kit. The kit comprises, or consists of, (a) a set of probes that enables diagnosis of bladder cancer, or monitoring of the recurrence thereof, in a patient and (b) instructions for diagnosing bladder cancer, or monitoring recurrence thereof, in a patient. The set of probes comprises, or consists of, a locus-specific probe for c-myc, a locus-specific probe for AURKA, a centromeric probe for chromosome 7, and a centromeric probe for chromosome 17. The instructions comprise determining in a sample of urothelial cells obtained from the patient the presence of chromosomal abnormalities, wherein the presence of chromosomal abnormalities involving at least two of the probes indicates that the patient has bladder cancer. Such kits may further comprise, or consist of, blocking agents or other probes, various labels or labeling agents to facilitate detection of the probes, reagents for hybridization (e.g., buffers), a metaphase spread, and the like.

EXAMPLE

The following example serves to illustrate the present invention. The example is not intended to limit the scope of the claimed invention in any way.

Example 1

This example describes the analysis of specimen slides using the probe set comprising a locus-specific probe for c-myc (8q24), a locus-specific probe for AURKA (20q13, specifically 20q13.2), a centromeric probe for chromosome 7, and a centromeric probe for chromosome 17.

Each sample of urothelial cells was placed in a ThinPrep vial (Hologic, Inc.), and PreservCyt (Hologic, Inc., Bedford, Mass.) was added to the vial to ensure a volume of 20 mL. A ThinPrep T-2000 processor (Hologic, Inc.) was used for sample preparation. Slides were prepared and soaked in 95% dehydrant for 30 minutes at room temperature. Afterwards, the slides were dried in a vertical position on a bench top for about 30 minutes to one hour before hybridization. Slides were evaluated under light microscope for cellularity and nuclear morphology.

The locus-specific probe for c-myc (8q24) was labeled red, whereas the locus-specific probe for AURKA (20q13) was labeled gold, the centromeric probe for chromosome 7 was labeled green, and the centromeric probe for chromosome 17 was labeled aqua.

The following protocol was used for fluorescent in situ hybridization (FISH). Slides were placed in 2×SSC at 72° C. for 2 minutes, 0.1-0.5 mg/ml pepsin (in 10 mM HCl) at 37° C. for 10 minutes, 1×PBS (phosphate-buffered saline) at room temperature for 5 minutes, 1% NBF at room temperature for 5 minutes, 1×PBS at room temperature for 5 minutes, 70% ethanol at room temperature for 1 minute, 85% ethanol at room temperature for 1 minute, and 100% ethanol at room temperature for 1 minute, and then air dried. After being air dried, each slide was contacted with 5 µL of probe mix and covered with an 18×18 mm cover slip. Slides were co-denatured at 73° C. for two minutes on a ThermoBrite Denaturation/Hybridization System (Abbott Molecular, Inc., Des Plaines, Ill.) and hybridized at 37° C. overnight (16-24 hours). Post-hybridization, slides were washed with 0.4×SSC with 0.3% NP40 for two minutes at 73° C. and 2×SSC with 0.1% NP40 for one minute at room temperature. DAPI II was then added to the slides, and the slides were covered with 24×30 mm cover slips. Slides were reviewed using fluorescence microscopy with red, gold, green, aqua and DAPI filters.

Slides were scanned using an Ikonisys automated scanning system (Ikonisys, Inc., New Haven, Conn.). The data are shown in Table I.

TABLE I

| Diagnosis | Diagnosis Rejected by Probe Panel | Diagnosis Confirmed by Probe Panel |
|---|---|---|
| High Grade (Histology-Biopsy)[1] | 2 | 18 |
| Low Grade (Histology-Biopsy)[1] | 3 | 24 |
| Low/High Grade (Histology-Biopsy) | 0 | 1 |
| PUNLMP (Histology-Biopsy)[2] | 0 | 4 |
| Negative (Histology-Biopsy) | 10 | 15 |
| Negative (Cytology) | 3 | 38 |
| Positive (Cytology) | 0 | 16 |
| Total | 18 | 116 |

[1]2004 World Health Organization (WHO) Classification
[2]papillary urothelial neoplasm of low malignant potential The sensitivity of the probe panel was 76.2% (48/63) (95% confidence interval) including PUNLMP as cancer, and 76.3% excluding PUNLMP as cancer. The specificity of the probe panel was 86.8% (46/53) (95% confidence interval).

Fifty two of 58 biopsy-confirmed specimens, which consisted of 21 high-grade, 28 low-grade, two not determined, and seven PUNLMP, were also tested using the probe panel. Diagnosis was confirmed for 47/52 specimens and rejected for 5/52 specimens.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:
1. A method of detecting bladder cancer in a human patient comprising:
   a) obtaining a sample of urothelial cells from a human patient;
   b) contacting the sample of urothelial cells with a set of detectably labeled probes consisting of a locus-specific probe for c-myc, which hybridizes to q24 on human chromosome 8, a locus-specific probe for AURKA, which hybridizes to q13 on human chromosome 20, a centromeric probe for human chromosome 7, and a centromeric probe for human chromosome 17, wherein each probe in the set is detectably labeled with a distinct fluorophore, and wherein the contacting is under conditions sufficient to enable hybridization of the probes in the set to target chromosomal sequences in the sample;
   c) detecting hybridization complexes formed between the detectably labeled probes in the set and target chromosomal sequences in the sample to thereby determine the copy number of c-myc at 8q24, AURKA at 20q13, chromosome 7 and chromosome 17; and
   d) detecting bladder cancer in the human patient based on gains or losses of copy number of c-myc at 8q24, AURKA at 20q13, chromosome 7 and chromosome 17 in the sample of urothelial cells as compared with pre-determined cut-off values.

2. The method of claim 1, wherein the patient has hematuria.

3. The method of claim 1, wherein the patient has been previously diagnosed with bladder cancer.

4. A method of monitoring the recurrence of bladder cancer in a human patient comprising:
   a) obtaining a sample of urothelial cells from a human patient who has previously had bladder cancer;
   b) contacting the sample of urothelial cells with a set of detectably labeled probes consisting of a locus-specific probe for c-myc, which hybridizes to q24 on human chromosome 8, a locus-specific probe for AURKA, which hybridizes to q13 on human chromosome 20, a centromeric probe for human chromosome 7, and a centromeric probe for human chromosome 17, wherein each probe in the set is detectably labeled with a distinct fluorophore, and wherein the contacting is under conditions sufficient to enable hybridization of the probes in the set to target chromosomal sequences in the sample;

c) detecting the number of hybridization complexes formed between the detectably labeled probes in the set and target chromosomal sequences in the sample to thereby determine the copy number of c-myc at 8q24, AURKA at 20q13, chromosome 7 and chromosome 17; and d) detecting recurrence of bladder cancer in the human patient based on gains or losses of copy number of c-myc at 8q24, AURKA at 20q13, chromosome 7 and chromosome 17 in the sample of urothelial cells as compared with pre-determined cut-off values.

5. A set of detectably labeled probes consisting of a locus-specific probe for c-myc, which hybridizes to q24 on human chromosome 8, a locus-specific probe for AURKA, which hybridizes to q13 on human chromosome 20, a centromeric probe for human chromosome 7, and a centromeric probe for human chromosome 17, wherein each probe is detectably labeled with a distinct fluorophore.

6. A kit consisting of (a) a set of detectably labeled probes that enables diagnosis of bladder cancer, or monitoring the recurrence thereof, in a patient, wherein the set of detectably labeled probes consists of a locus-specific probe for c-myc, which hybridizes to q24 on human chromosome 8, a locus-specific probe for AURKA, which hybridizes to q13 on human chromosome 20, a centromeric probe for human chromosome 7, and a centromeric probe for human chromosome 17 and wherein each probe is detectably labeled with a distinct fluorophore; (b) instructions for diagnosing bladder cancer, or monitoring recurrence thereof, in a patient, wherein the instructions comprise an instruction to contact a sample of urothelial cells obtained from the human patient with the set of detectably labeled probes under hybridization conditions and an instruction to determine in the sample of urothelial cells the presence of chromosomal abnormalities; and optionally (c) one or more items selected from the group consisting of a blocking agent, a label, a labeling agent, a reagent for hybridization, a buffer, and a metaphase spread; wherein the presence of chromosomal abnormalities involving at least two of c-myc, AURKA, chromosome 7, and chromosome 17 indicates that the patient has bladder cancer.

* * * * *